United States Patent
Yang (10) Patent No.: US 12,427,244 B2
(45) Date of Patent: Sep. 30, 2025

(54) UNILATERAL-DRIVEN PATCH-TYPE DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 725 days.

(21) Appl. No.: 17/785,406

(22) PCT Filed: Sep. 8, 2020

(86) PCT No.: PCT/CN2020/113980
§ 371 (c)(1),
(2) Date: Jun. 15, 2022

(87) PCT Pub. No.: WO2021/135359
PCT Pub. Date: Jul. 8, 2021

(65) Prior Publication Data
US 2023/0022657 A1 Jan. 26, 2023

(51) Int. Cl.
*A61M 5/142* (2006.01)
*A61B 5/00* (2006.01)
(Continued)

(52) U.S. Cl.
CPC ....... *A61M 5/14248* (2013.01); *A61B 5/4839* (2013.01); *A61M 5/14216* (2013.01);
(Continued)

(58) Field of Classification Search
CPC ...... A61M 2005/14506; A61M 5/1454; A61M 5/14248; A61M 2005/14252;
(Continued)

(56) References Cited

U.S. PATENT DOCUMENTS

2003/0236498 A1* 12/2003 Gross ............... A61M 5/14216
604/141
2008/0051738 A1* 2/2008 Griffin ................ A61M 5/158
604/272
(Continued)

FOREIGN PATENT DOCUMENTS

CN 101208515 A * 6/2008
CN 103007381 4/2013
(Continued)

OTHER PUBLICATIONS

"International Search Report (Form PCT/ISA/210) of PCT/CN2020/113980," mailed on Dec. 2, 2020, pp. 1-35.
(Continued)

*Primary Examiner* — Jason E Flick
*Assistant Examiner* — Isabella S North
(74) *Attorney, Agent, or Firm* — JCIPRNET (57) ABSTRACT

A unilateral-driven patch-type drug infusion device, includes: an infusion unit, which includes a drug storage unit; a screw connected to a piston and a driving wheel provided with wheel teeth, respectively, the driving wheel drives the screw to move by rotation, pushing the piston forward; at least one driving unit cooperating with the driving wheel, the driving unit includes at least one driving portion; a power unit and a reset unit coupled to the driving unit, and an infusion tube structure, which includes a base and an infusion needle, and the base includes an initial position, a working position, and an intermediate position. This infusion device can output controllable and stable driving force, which eliminates safety hazards and improves user experience.

19 Claims, 8 Drawing Sheets

(51) Int. Cl.
*A61M 5/145* (2006.01)
*A61M 5/158* (2006.01)
*A61M 5/168* (2006.01)
*A61M 5/172* (2006.01)
*A61M 5/36* (2006.01)
*B25B 13/46* (2006.01)
*B25B 23/00* (2006.01)

(52) U.S. Cl.
CPC .......... *A61M 5/1452* (2013.01); *A61M 5/158* (2013.01); *A61M 5/1684* (2013.01); *A61M 5/16877* (2013.01); *A61M 5/172* (2013.01); *A61M 5/36* (2013.01); *B25B 13/463* (2013.01); *A61B 2560/0209* (2013.01); *A61B 2562/043* (2013.01); *A61M 2005/14208* (2013.01); *A61M 2005/14252* (2013.01); *A61M 2005/14268* (2013.01); *A61M 2005/14533* (2013.01); *A61M 2205/0266* (2013.01); *A61M 2205/106* (2013.01); *A61M 2205/3317* (2013.01); *A61M 2205/3576* (2013.01); *A61M 2205/50* (2013.01); *B25B 23/0078* (2013.01)

(58) Field of Classification Search
CPC ...... A61M 5/1452; A61M 5/158; A61M 5/36; A61M 5/14236; A61M 5/14212; A61M 5/1582; A61M 2005/14533

USPC ........................................................ 604/152
See application file for complete search history.

(56) References Cited

U.S. PATENT DOCUMENTS

| | | |
|---|---|---|
| 2009/0093792 A1 | 4/2009 | Gross et al. |
| 2009/0105650 A1 | 4/2009 | Wiegel et al. |
| 2010/0152660 A1* | 6/2010 | Mack ...................... A61M 5/20 |
| | | 604/173 |
| 2013/0296789 A1 | 11/2013 | Mernoe et al. |
| 2016/0175527 A1* | 6/2016 | Mccullough ...... A61M 5/31501 |
| 2019/0009019 A1 | 1/2019 | Shor et al. |
| 2019/0117881 A1 | 4/2019 | Yang |

FOREIGN PATENT DOCUMENTS

| | | | |
|---|---|---|---|
| CN | 106110445 | 11/2016 | |
| CN | 106110445 A * | 11/2016 | .............. A61M 5/19 |
| CN | 106139311 | 11/2016 | |
| WO | 2012055771 | 5/2012 | |
| WO | WO-2017134966 A1 * | 8/2017 | ............ A61M 5/158 |
| WO | WO-2017181324 A1 * | 10/2017 | ............ A61M 5/142 |

OTHER PUBLICATIONS

"Search Report of Europe Counterpart Application", issued on Feb. 22, 2024, p. 1-p. 10.

* cited by examiner

FIG.12

UNILATERAL-DRIVEN PATCH-TYPE DRUG INFUSION DEVICE

CROSS-REFERENCE TO RELATED APPLICATION

This application is a 371 of international application of PCT application serial no. PCT/CN2020/113980, filed on Sep. 8, 2020, which claims the priority benefit of PCT application no. PCT/CN2019/130442, filed on Dec. 31, 2019. The entirety of each of the above-mentioned patent applications is hereby incorporated by reference herein and made a part of this specification.

TECHNICAL FIELD

The present invention mainly relates to the field of medical instruments, in particular to a unilateral-driven patch-type drug infusion device.

BACKGROUND

A drug infusion device can continuously deliver drug into a patient's body for disease treatment. Drug infusion devices are widely used in the field of diabetes treatment, which continuously infuse required dosage of insulin into the patient's subcutaneous tissue, thereby simulating the secretion function of the pancreas to keep the blood glucose stable. The drug fluid is usually stored inside the infusion pump. The drug infusion device in prior art, controlled by remote device, is usually attached directly on the patient's skin through a medical adhesive tape.

At present, drug infusion devices in prior art have insufficient driving force, thus, drugs cannot be infused into the body in time. And air maybe infused in subcutaneous, which affects the health of users and poses safety risks.

Therefore, in the prior art, there is an urgent need for a unilateral-driven patch-type drug infusion device which can not only output larger infusion driving force, but also prevent air from being infused into subcutaneous.

BRIEF SUMMARY OF THE INVENTION

Embodiments of the present invention provide a unilateral-driven patch-type drug infusion device. The power unit can output controllable and stable driving force to drive the driving portion forward, thereby pushing the wheel teeth forward, avoiding drug blockage. At the same time, when the infusion tube structure is at intermediate position, the drug can exhaust the air from the infusion needle, preventing air from being infused into subcutaneous, which eliminates safety hazards and improves user experience.

The invention discloses a unilateral-driven patch-type drug infusion device, comprising: an infusion unit, which includes a drug storage unit providing with an opening for drug flowing; a screw connected to a piston and a driving wheel provided with wheel teeth, respectively, the driving wheel drives the screw to move by rotation, thereby pushing the piston, provided in the drug storage unit, forward; at least one driving unit cooperating with the driving wheel, the driving unit includes at least one driving portion; a power unit and a reset unit coupled to the driving unit, wherein: when the power unit outputs force on the driving unit, the driving unit rotates around a pivot shaft, driving the driving portion to push the wheel teeth, thus rotating the driving wheel; when the reset unit outputs a force on the driving unit alone, the driving unit performs a reset rotation without the driving portion pushing the wheel teeth, thus making the driving wheel stop rotating; a housing, where the infusion unit is provided, includes a cavity providing with a first outlet and a second outlet, the opening is in sealed communication with the first outlet while the second outlet is sealed by an elastic seal; an infusion tube structure, which includes a base and an infusion needle fixedly arranged on the base, and the base includes an initial position, a working position, and an intermediate position set between the initial position and the working position; and a first fastener, which is used to fasten the base in order to limit the position of the base.

According to one aspect of this invention, the driving unit includes two driving portions, and under the cooperative operation of the power unit and the reset unit, the two driving portions can alternately push the wheel teeth.

According to one aspect of this invention, the two driving portions alternately push the wheel teeth disposed on the same driving wheel.

According to one aspect of the present invention, the driving wheel includes two sub-wheels provided with wheel teeth, and the two driving portions respectively alternately push the wheel teeth disposed on different sub-wheels.

According to one aspect of the invention, the power unit and the reset unit are linear actuator.

According to one aspect of the invention, the linear actuator includes a shape memory alloy.

According to one aspect of the present invention, the reset unit at least includes a spring, an elastic sheet, an elastic plate, an elastic rod, or elastic reset rubber.

According to one aspect of the present invention, the driving unit includes one driving portion, and the reset unit is a spring.

According to one aspect of the present invention, the type of the first fastener includes one or more of hooks, holes, blocks, or slots.

According to one aspect of the present invention, it further includes an elastic member arranged on the base or the housing, and when the base is in the working position, the elastic member is compressed.

According to one aspect of the present invention, it further includes an auxiliary resilient component, which is used to release the base, therefore under the action of the resilient force of the elastic member, the base returns to the intermediate position or the initial position from the working position.

According to one aspect of the present invention, the base includes a guide post, and the position where the base is fastened is located on the guide post.

According to one aspect of the present invention, the elastic member is a spring arranged on the housing, and a part of the guide post is located in the hollow cavity of the spring.

According to one aspect of the present invention, the first fastener is provided on the housing.

According to one aspect of the present invention, it further includes a fastening component, and the first fastener is disposed on the fastening component.

According to one aspect of the present invention, a sliding block is provided on the fastening component while the housing is provided with a groove, the sliding block is arranged in the groove, and the sliding block can slide along the groove to make the fastening component fasten or release the base.

According to one aspect of the present invention, at least one fastening arm is provided on the fastening component, and the first fastener is provided on the fastening arm.

According to one aspect of the present invention, a second fastener is provided on the housing, the first fastener is used to fasten the base at the initial position or the intermediate position while the second fastener is used to fasten the base at the work position.

According to one aspect of the present invention, the infusion needle includes a front end and a subcutaneous end, both the front end and the subcutaneous end extend out of the base, wherein: when the base is at the initial position, the front end is not communicated with the second outlet; when the base reaches the intermediate position or the working position, the front end pierces the elastic seal to communicate with the second outlet, and the drug, along the cavity, flows from the drug storage unit to the subcutaneous end.

Compared with the prior arts, the technical solution of the present invention has the following advantages:

In the unilateral-driven patch-type drug infusion device disclosed herein, at least one driving unit cooperating with the driving wheel, the driving unit includes at least one driving portion; a power unit and a reset unit coupled to the driving unit, when the power unit outputs a force on the driving unit, the driving unit rotates around a pivot shaft, driving the driving portion to push the wheel teeth, thus rotating the driving wheel; when the reset unit outputs a force on the driving unit alone, the driving unit performs a reset rotation without the driving portion pushing the wheel teeth, thus making the driving wheel stop rotating. The power unit can provide a sufficiently great and stable driving power, which in turn enables the drug infusion device to have a sufficiently great and stable infusion pressure to avoid drug blockage. At the same time, the infusion tube structure includes a base and an infusion needle fixedly arranged on the base, and the base includes an initial position, a working position, and an intermediate position set between the initial position and the working position. Setting an intermediate position between the initial position and the working position makes the infusion needle filled with drug before it enters subcutaneous, preventing air from entering the subcutaneous, therefore, eliminating potential safety hazards.

Furthermore, the driving unit includes two driving portions, and under the cooperative operation of the power unit and the reset unit, the two driving portions can alternately push the wheel teeth. Two driving portions pushing the wheel teeth alternately can not only improve the infusion efficiency but also make the infusion device have multiple infusion modes.

Furthermore, the reset unit and the power unit are linear actuator. The force of the linear actuator can be controlled by current. When the current is constant, the force output by the linear actuator is constant. Therefore, the linear actuator can output stable and controllable force, thus making the drug infusion proceed smoothly.

Furthermore, the reset unit at least includes a spring, an elastic sheet, an elastic plate, an elastic rod, or an elastic reset rubber. The reset unit can work without consuming additional energy, which reduces the power consumption of the drug infusion device and saves the production cost.

Furthermore, the infusion device also includes an elastic member, which is arranged on the base or on the housing, and when the base is in the working position, the elastic member is compressed. Before the infusion device is torn off, the subcutaneous end of the infusion needle can be retracted into the housing by the elastic member to avoid scratching the skin and improve user experience.

BRIEF DESCRIPTION OF THE DRAWINGS

FIG. 4b is the top view of FIG. 4a.

FIG. 8b is a schematic view of the driving unit in FIG. 8a.

DETAILED DESCRIPTION

As mentioned above, the infusion device in prior art is prone to drug blockage, so that the drug cannot be infused into the body in time. Air will enter the subcutaneous, which affects the user's health and poses a safety hazard.

Studies have found that the reasons for the above problems are: the driving force for drug infusion is the resilience of the elastic component which is easy to change and whose stability is uncontrollable. And air exists in the cavity of the infusion needle when it penetrates into subcutaneous.

In order to solve this problem, the present invention provides a unilateral-driven patch-type drug infusion device. The power unit outputs a controllable driving force to drive the driving portion forward, thereby pushing the wheel teeth forward, avoiding the drug blockage. At the same time, when the infusion tube structure is at intermediate position, the drug can exhaust the air in the infusion needle, preventing air from being infused into subcutaneous, which eliminates safety hazards and improves user experience.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

Figure 1:
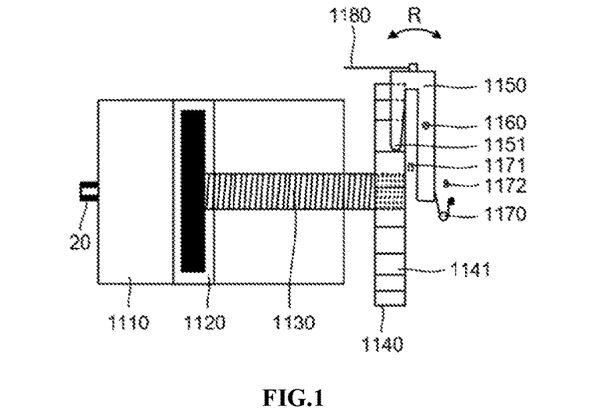
FIG. 1 is a schematic view of the main structures in the infusion unit according to an embodiment of the present invention.

FIG. 1 is a schematic view of main structures in the infusion unit according to an embodiment of the present invention.

The internal structure of the infusion unit mainly includes a drug storage unit 1110, a piston 1120, a screw 1130, a driving wheel 1140, at least one driving unit 1150, a pivot shaft 1160, a reset unit 1170, a power unit 1180 and an infusion tube. The infusion tube will be described in detail below. In the embodiment of this present invention, the driving unit 1150 is coupled with the reset unit 1170 and the power unit 1180, respectively. It should be noted that the coupling herein includes mechanical connection or electrical connection.

The drug storage unit 1110 is used for storing liquid drug. Drugs include, but are not limited to, insulin, glucagon, antibiotics, nutrient solutions, analgesics, morphine, anticoagulants, gene therapy drugs, cardiovascular drugs or chemotherapy drugs, etc. Preferably, in the embodiment of this present invention, the drug is insulin.

The piston 1120 is used to infuse drugs into the body.

The screw 1130 is connected to the piston 1120 and the driving wheel 1140, respectively. In the embodiment of the present invention, the driving wheel 1140 advances the screw 1130 forward by screwing, the screw 1130 then forces the piston 1120, arranged in the drug storage unit 1110, to move forward, so as to achieve the purpose of insulin infusion.

The peripheral surface of the driving wheel 1140 is provided with wheel teeth 1141. The wheel teeth 1141 are gear teeth or ratchet teeth. Preferably, in the embodiment of the present invention, for improving driving efficiency, the wheel teeth 1141 are ratchet teeth which can be pushed more easily.

At least one driving portion 1151 is provided on the driving unit 1150 to push the wheel teeth 1141, thereby rotating the driving wheel 1140. The driving unit 1150 is movably connected to the pivot shaft 1160. Preferably, in the embodiment of the present invention, the driving unit 1150 includes one driving portion 1151.

The power unit 1180 and the reset unit 1170 are controlled by the program unit and cooperate with each other to make the driving unit 1150 rotate reciprocally around the pivot shaft 1160, as shown in the R direction in FIG. 1, thereby making the driving portion 1151 move in the advancing direction and reset direction. When the driving unit 1150 performs one reciprocating rotation, the driving wheel 1140 drives the screw 1130 forward one step, and the screw 1130 engages the piston 1120 to infuse one unit of insulin.

It should be noted here that the advancing direction of the driving portion 1151 refers to the direction in which the wheel teeth 1141 moves, while the reset direction of the driving portion 1151 is opposite to the advancing direction. During the reset movement, the driving portion 1151 only slides on the surface of the wheel teeth 1141 without pushing them.

In some embodiments of the present invention, the reset unit 1170 at least includes a spring, an elastic piece, an elastic plate, an elastic rod, rubber and other elastic components. Preferably, the reset unit 1170 is a spring. It should be noted that the spring herein includes a compression spring, an extension spring, or a torsion spring, etc. Preferably, in the embodiment of the present invention, the reset unit 1170 is a torsion spring which is more conducive to the reset of the driving unit 1150. When the reset unit 1170 is an elastic member, it can work without consuming additional energy, which reduces the power consumption of the infusion unit and saves the production cost.

In other embodiments of the present invention, the reset unit 1170 includes an electrically driven linear actuator or an electrically heated linear actuator, such as a shape memory alloy. After being energized, the physical form of the material of the linear actuator, like shape memory alloy, changes, which makes shrinkage deformation of the shape memory alloy occur, thereby outputting the driving force. The higher the current is, the larger the shrinkage deformation of the shape memory alloy occurs, and the greater the driving force outputs. Obviously, when the current is constant, the shrinkage deformation of the linear actuator is also constant, so the driving force is. Therefore, the shape memory alloy can output stable and controllable driving force for insulin infusion.

The type, material selection or the position of the reset unit 1170 are not specifically limited herein, as long as it can satisfy the condition of making the driving unit 1150 rotate in the reset direction.

The power unit 1180 is an electrically driven linear actuator or an electrically heated linear actuator. By alternately turning on and off, the power unit 1180 outputs force in pulses. Preferably, in the embodiment of the present invention, the power unit 1180 is a shape memory alloy.

Figure 2A:
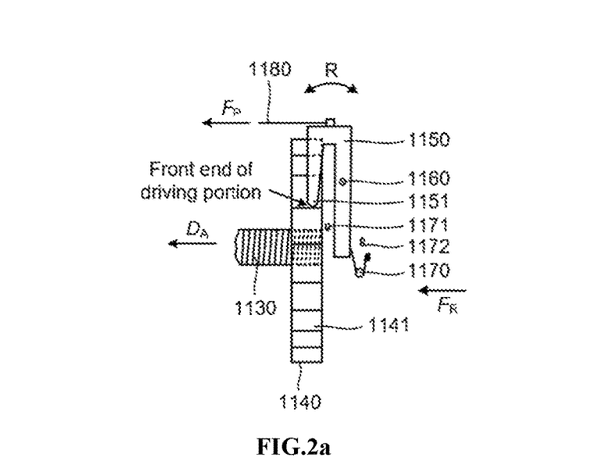
FIG. 2a-FIG. 2c are top views of the driving portion pushing the wheel teeth according to different embodiments of the present invention.
Figure 2B:
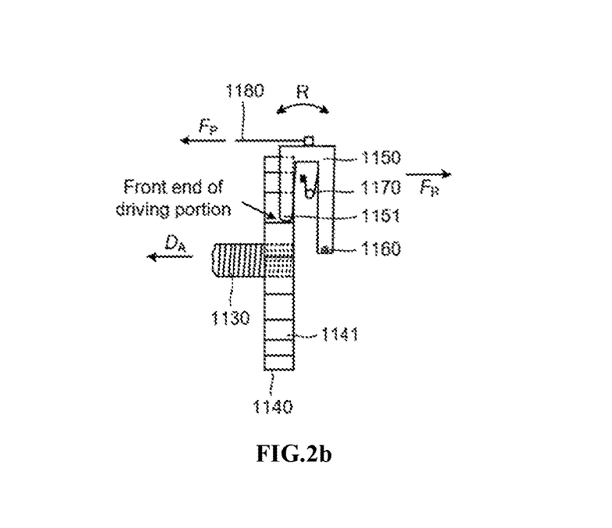
Figure 2C:
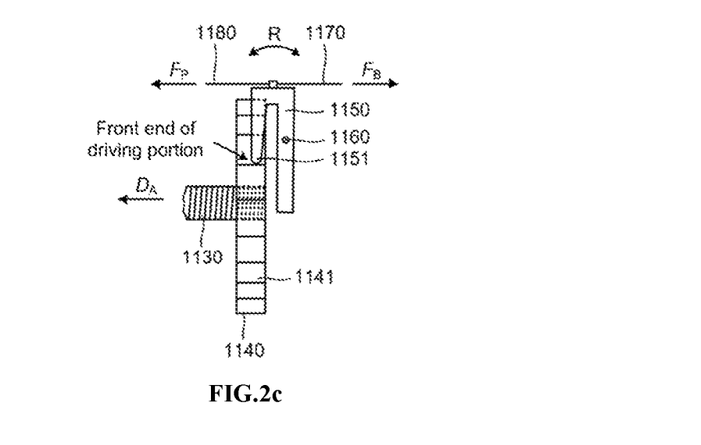
Figure 3A:
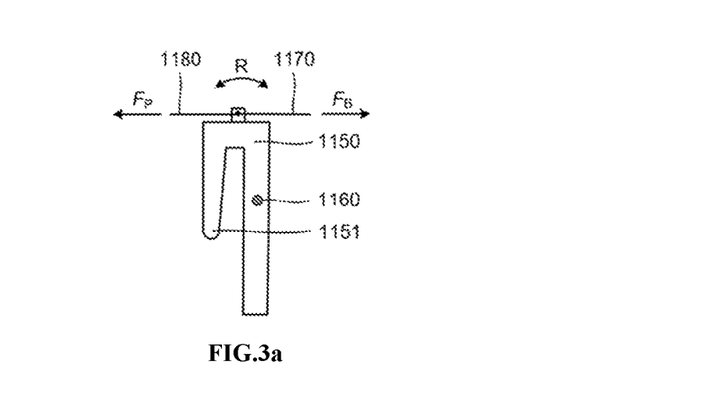
FIG. 3a-FIG. 3c are schematic views of the power unit, the reset unit and the driving unit cooperating with each other according to different embodiments of the present invention.
Figure 3B:
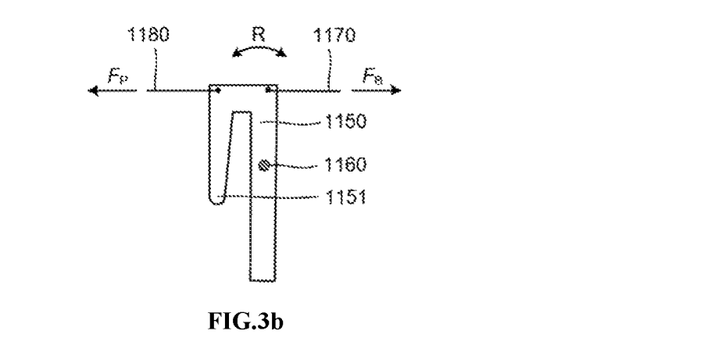
Figure 3C:
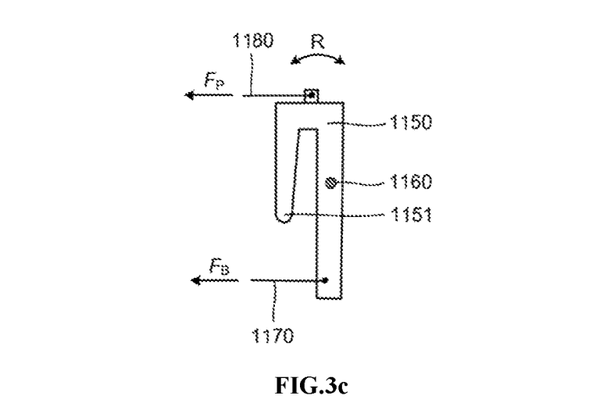

FIG. 2*a*-FIG. 2*c* are top views of the driving portion 1151 pushing the wheel teeth 1141 in different embodiments of the present invention. FIG. 3*a*-FIG. 3*c* are schematic views of the power unit 1180, the reset unit 1170 and the driving unit 1150 cooperating with each other in different embodiments of the present invention.

As shown in FIG. 2*a* and FIG. 2*b*, the principle of the reciprocating rotation of the driving unit 1150 in the embodiment of the present invention is as follows. When the power unit 1180 pulls the driving unit 1150 by force $F_P$, the driving unit 1150 rotates counter-clockwise (advancing direction) around the pivot shaft 1160, driving the driving portion 1151 to push the wheel teeth 1141 forward, and thereby making the driving wheel 1140 rotate. The driving wheel 1140 then moves the screw 1130 forward in $D_A$ direction. The reset unit 1170, as an elastic member, builds a gradually increasing elastic force $F_R$. When the power unit 1180 stops applying force and under the action of only the elastic force $F_R$, the driving unit 1150 will rotate clockwise (reset direction) around the pivot shaft 1160. At this time, the driving portion 1151 just slides on the surface of the wheel teeth 1141 instead of pushing them, therefore the driving wheel 1140 stops rotating. The driving unit 1150 completes one reciprocating rotation.

As shown in FIG. 2b, in another embodiment of the present invention, the reset unit 1170 and the power unit 1180 are disposed on the same side of the pivot shaft 1160. And according to the general technical principles, those skilled in the art can arbitrarily adjust the positional relationship and the connection relationship of the reset unit 1170, the driving unit 1150, and the power unit 1180, which is not specifically limited herein, as long as the abovementioned rotation processes can be achieved.

As shown in FIG. 2c, in yet another embodiment of the present invention, the reset unit 1170 includes an electrically driven linear actuator or an electrically heated linear actuator, such as a shape memory alloy. Although the technical principle that the driving portion 1151 pushes the wheel teeth 1141 is consistent with the foregoing, the driving unit 1150 cannot automatically reset after the driving portion 1151 stops advancing, therefore, the reset unit 1170 is required to provide the reset force $F_B$ whose direction is opposite with that of $F_P$, thereby making the driving unit 1150 rotate reciprocally with the cooperation of the reset unit 1170 and the power unit 1180.

Preferably, as shown in FIG. 2a to FIG. 2c, in the embodiment of the present invention, the directions of $F_P$, $F_R$ (or $F_B$) and $D_A$ are parallel to one another. This parallel design can make full use of space and optimize the structural relationships inside the infusion unit, making internal structure more compact.

Obviously, those skilled in the art can arbitrarily adjust the directions of the $F_P$ and $F_B$ as needed, as long as the conditions for reciprocating rotation of the driving unit 1150 are satisfied, as shown in FIG. 3a-FIG. 3c.

In other embodiments of the present invention, the direction of $F_P$ and the direction of $F_R$ (or $F_B$) or the direction of $D_A$ may not be parallel, which is not specifically limited herein, as long as the purpose of the reciprocating rotation of the driving unit 1150 can be achieved.

Figure 4A:
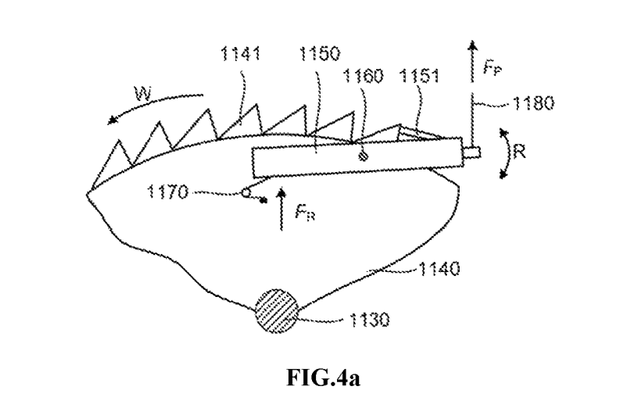
FIG. 4a-FIG. 4b are schematic views of that the pulling direction of the power unit is not parallel to the advancing direction of the screw according to another embodiment of the present invention.
Figure 4B:
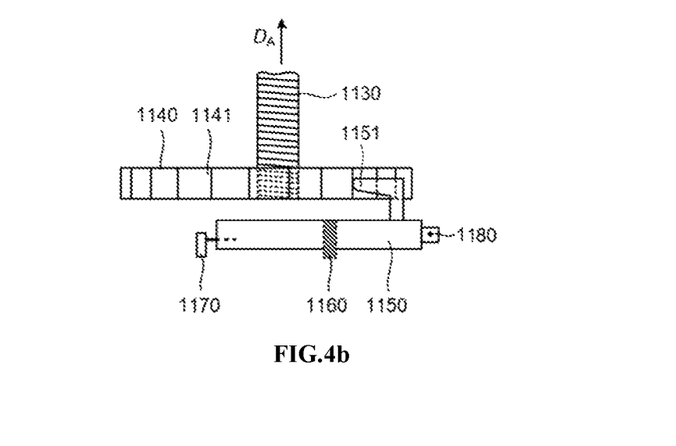

FIG. 4a-FIG. 4b are schematic views of that the pulling direction of the power unit 1180 is not parallel to the advancing direction of the screw 1130. FIG. 4b is the top view of FIG. 4a.

The $F_P$ direction of the power unit 1180 is perpendicular to the forward direction $D_A$ of the screw 1130. The pivot shaft 1160 and the reset unit 1170 are disposed on the base. As described above, the driving unit 1150, rotating reciprocally in the R direction, drives the driving portion 1151 to push the wheel teeth 1141, making the driving wheel 1140 rotate in the W direction and driving the screw 1130 to advance in the $D_A$ direction. The driving principle of the driving unit 1150 is consistent with the foregoing embodiment.

In the embodiment of the present invention, blocking walls 1171 and 1172 (as shown in FIG. 1 and FIG. 2a) that can stop the driving unit 1150 from rotating are also provided in the infusion unit. And an electrical signal may be triggered when the driving unit 1150 contacts the blocking wall 1171 or 1172, allowing the program unit to control the driving force output of the power unit 1180. In another embodiment of the present invention, only the blocking wall 1171 or only the blocking wall 1172 may be provided, so that the rotating terminal in either direction of the driving unit 1150 is controlled by the program unit. The position of the blocking wall 1171 or 1172 is not specifically limited herein, as long as the condition that the driving unit 1150 stops rotating can be satisfied.

In another embodiment of the present invention, no blocking wall is provided (as shown in FIG. 2b to FIG. 4b), and the rotating terminal of the driving unit 1150 is completely controlled by the program unit.

Figure 5:
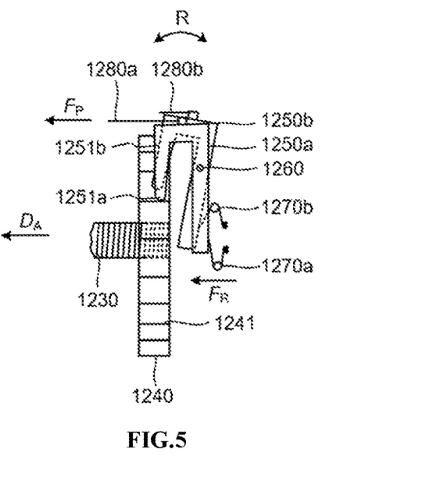
FIG. 5 is a schematic view of the infusion unit including two driving units according to an embodiment of the present invention.
Figure 6:
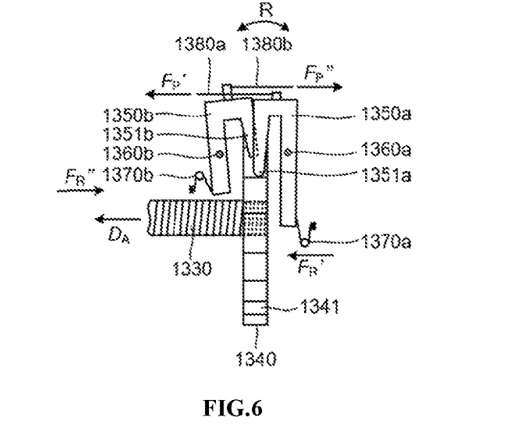
FIG. 6 is a schematic view of the infusion unit including two driving units according to another embodiment of the present invention.

FIG. 5 and FIG. 6 are schematic views of the infusion unit including two driving units according to different embodiments of the present invention.

As shown in FIG. 5, the driving unit 1250a rotates reciprocally in the R direction around the pivot shaft 1260 under the action of the power unit 1280a and the reset unit 1270a. Similarly, the driving unit 1250b rotates reciprocally in the R direction around the pivot shaft 1260 under the action of the power unit 1280b and the reset unit 1270b. In the embodiment of the present invention, the reciprocating rotations of the two driving units do not interfere with each other. Therefore, both the driving unit 1250a and the driving unit 1250b can independently implement the driving method or principle described above.

Preferably, in the embodiment of the present invention, the driving unit 1250a and the driving unit 1250b rotate asynchronously. That is, when the driving portion 1251a of the driving unit 1250a pushes the wheel teeth 1241 to move, the driving portion 1251b of the driving unit 1250b slides on the surface of the wheel teeth 1241. When the driving portion 1251b slides to one position, the program unit controls the power unit 1280a to stop outputting driving power to the driving unit 1250a, and in turn controls the power unit 1280b to output power to the driving unit 1250b. At this time, the driving unit 1250a rotates in the clockwise direction under the action of the reset unit 1270a, and the driving portion 1251a slides on the surface of the wheel teeth, while the driving portion 1251b pushes the wheel teeth 1241. The driving units 1250a and 1250b are alternately powered to push the same driving wheels 1240. Two driving portions pushing the wheel teeth alternately can not only improve the infusion efficiency, but also make the infusion unit have multiple infusion modes.

In the embodiment of the present invention, the pulling force $F_P$ of the power units 1280a and 1280b, the elastic force $F_R$ of the reset units 1270a and 1270b and the forward direction $D_A$ of the screw 1230 are shown in the figures. Like foregoing statement, the direction of the pulling force $F_P$ is parallel to the forward direction $D_A$ of the screw 1230.

In the embodiment of the present invention, the types of the reset units 1270a and 1270b can be referred to the above, which will not be repeated herein.

As shown in FIG. 6, the driving portions 1351a and 1351b alternately push the wheel teeth 1341, respectively, and the force output by the power units 1380a and 1380b are both controlled by the program unit.

It should be noted that, in the embodiment of the present invention, the direction of the pulling force $F_P'$ of the power unit 1380a and that of the pulling force $F_P''$ of the power unit 1380b are opposite. Obviously, the direction of the resetting force $F_R'$ of the reset unit 1370a and that of the resetting force $F_R''$ of the reset unit 1370b are also opposite.

Also, in the embodiment of the present invention, the driving units 1350a and 1350b rotate asynchronously. That is, when the driving portion 1351a of the driving unit 1350a pushes the wheel teeth 1341 forward, the driving portion 1351b of the driving unit 1350b slides on the surface of the wheel teeth 1341. When the driving portion 1351b slides to one position, the program unit controls the power unit 1380a to stop outputting power to the driving unit 1350a, and in turn controls the power unit 1380b to output power to the driving unit 1350b. The driving unit 1350a resets to the clockwise rotation by the reset unit 1370a, while the driving portion 1351a slides on the surface of the wheel teeth 1341, and the driving portion 1351b pushes the wheel teeth 1341. The driving units 1350a and 1350b alternately pushes the driving wheels 1340.

Similarly, both the driving unit 1350a and the driving unit 1350b can independently implement the driving method or principle described above. And the types of the reset units 1370a and 1370b can be referred to the above, which will not be repeated herein.

It should be noted that, in other embodiments of the present invention, more driving units can be arranged in the infusion unit, or more driving portions are disposed on each driving unit, or the driving wheel includes more sub-wheels. Therefore, different driving units respectively push the corresponding sub-wheels to rotate.

Figure 7A:
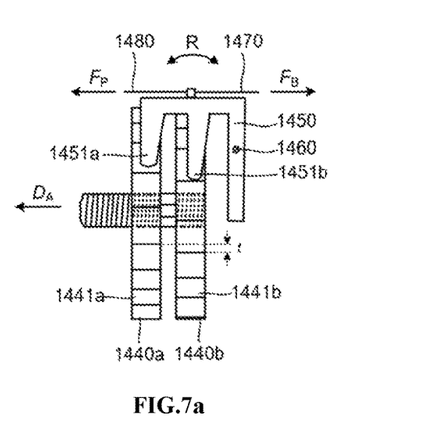
FIG. 7a-FIG. 7b are schematic views of two driving portions of one driving unit cooperating with two sub-wheels respectively according to yet another embodiment of the present invention.
Figure 7B:
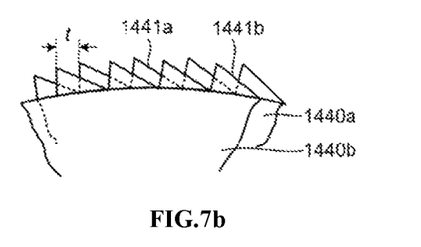

FIG. 7a and FIG. 7b are schematic views of two driving portions 1451a and 1451b of one driving unit 1450 cooperating with two sub-wheels 1440a and 1440b, respectively according to yet another embodiment of the present invention. FIG. 7b is a right view of the partial teeth structure of the sub-wheels 1440a and 1440b in FIG. 7a.

As shown in FIG. 7a and FIG. 7b, in the embodiment of the present invention, the driving unit 1450 includes two driving portions 1451a and 1451b disposed left and right, while the driving wheel includes two fixedly connected sub-wheels 1440a and 1440b disposed on the left and right (that is, two sub-wheels can move simultaneously). The driving portions 1451a and 1451b cooperate with the sub-wheels 1440a and 1440b, respectively, and the pivot shaft 1460 is disposed on the same side of two sub-wheels 1440a and 1440b. Both the power unit 1480 and the reset unit 1470 of the embodiment of the present invention are shape memory alloys, and the driving portion 1451a or 1451b can respectively push the wheel teeth 1441a or 1441b forward. Their working principles and operating modes are consistent with the foregoing embodiments.

In addition to driving portion 1451a or 1451b operating independently, the embodiment of the present invention can also adjust the distance between the front ends of the driving portions 1451a and 1451b, or adjust the offset degree of the wheel teeth 1441a and 1441b to make two driving portions 1451a and 1451b cooperate with each other. Preferably, in the embodiment of the present invention, the wheel teeth 1441a and 1441b are offset with degree t, as shown in FIG. 7a and FIG. 7b.

Obviously, in the embodiment of the present invention, two driving portions 1451a and 1451b reciprocate synchronously. As shown in FIG. 7a, when the previous forward movement is completed, the driving unit 1450 starts a reset rotation, the driving portion 1451a reaches the driving position before the driving portion 1451b, so the driving portion 1451a can be used to start the next forward movement instead. Or the driving unit 1450 continues the reset movement until the driving portion 1451b reaches the next driving position to start the next forward movement.

Figure 8A:
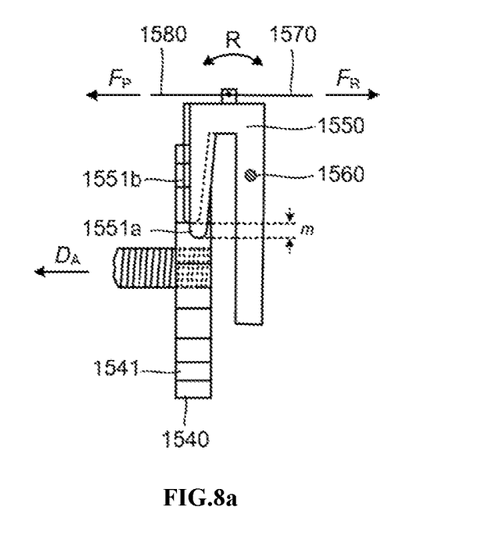
FIG. 8a-FIG. 8b are schematic views of two driving portions of one driving unit cooperate with the same driving wheel according to yet another embodiment of the present invention.
Figure 8B:
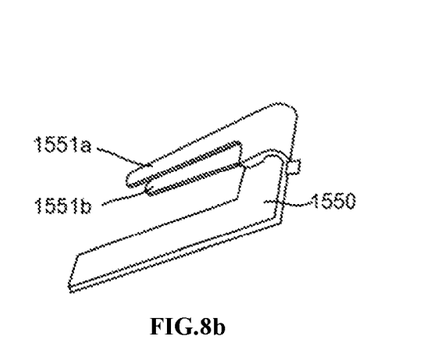

FIG. 8a and FIG. 8b are still another embodiment of the present invention in which the driving unit 1550 includes two driving portions 1551a and 1551b disposed up and down, and driving portions 1551a and 1551b cooperate with the same driving wheel 1540. FIG. 8b is a schematic view of the driving unit 1550 in FIG. 8a.

As shown in FIG. 8a and FIG. 8b, the driving unit 1550 includes two driving portions 1551a and 1551b disposed up and down cooperating with the same driving wheel 1540, so the driving portions 1551a and 1551b reciprocate synchronously. The front ends of the driving portions 1551a and 1551b are not level with a certain distance m, therefore, the two cannot simultaneously push the wheel teeth 1541 forward, as shown in FIG. 8a. When the driving portion 1551b finishes the last forward movement, the driving unit 1550 performs a reset movement, obviously making the driving portion 1551a reach the next driving position before the driving portion 1551b. The driving portion 1551a can be used to push the wheel teeth 1541 forward to start the next forward movement.

In other embodiments of the present invention, the driving unit may further include more driving portions, such as 3, 4 or more, which is not specifically limited herein.

Figure 9A:
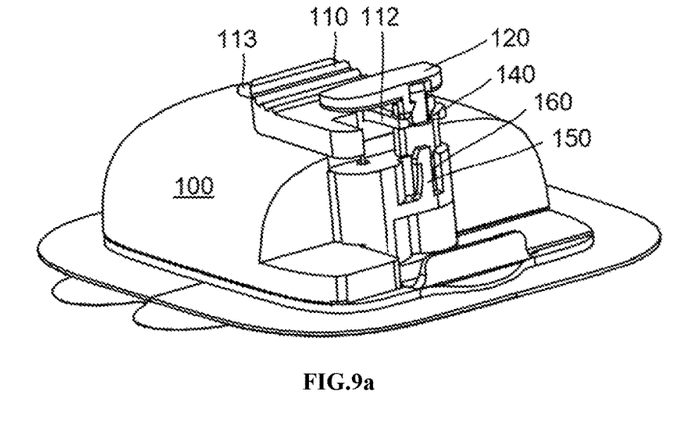
FIG. 9a is a schematic view of a part of the structure of the infusion device according to an embodiment of the present invention.
Figure 9B:
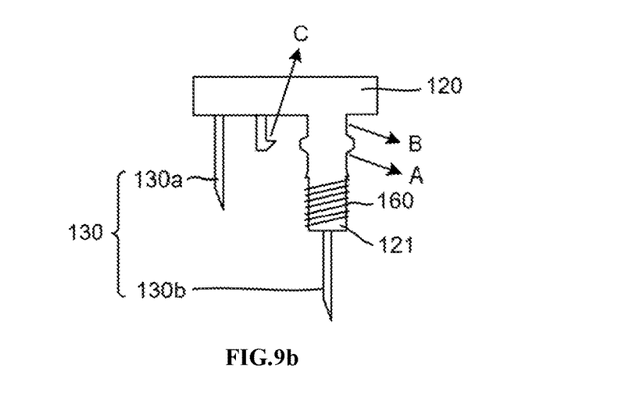
FIG. 9b is a schematic view of an infusion tube structure according to an embodiment of the present invention.
Figure 9C:
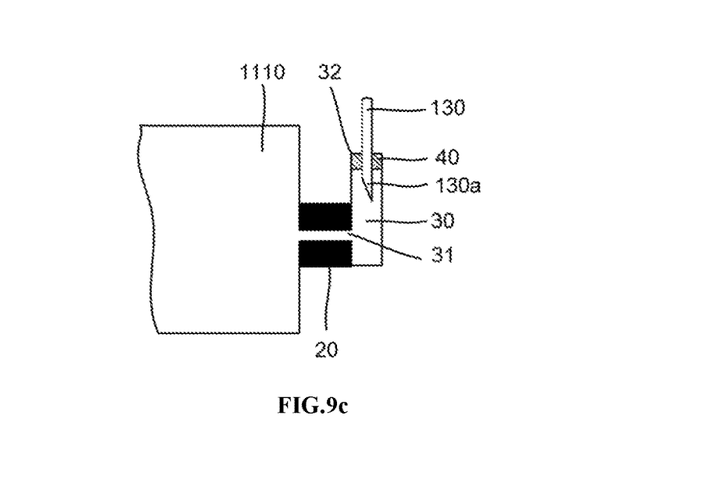
FIG. 9c is a schematic view of the drug storage unit and the cavity according to the embodiment of this present invention.

FIG. 9a is a schematic view of a part of the structure of the infusion device according to an embodiment of this present invention. FIG. 9b is a schematic view of an infusion tube structure according to an embodiment of this present invention. FIG. 9c is a schematic view of the drug storage unit 1110 and the cavity 30 according to the embodiment of the present invention.

As shown in FIG. 9a, the infusion device of the embodiment of the present invention includes a housing 100 where the infusion unit is provided. The infusion tube structure, arranged on the housing 100, is used to fixedly place the infusion needle 130, making the drug flow into subcutaneous.

As shown in FIG. 9b, the infusion tube structure includes an infusion needle 130 and a base 120. The infusion needle 130 is fixedly placed on the base 120. The infusion needle 130 includes a front end 130a and a subcutaneous end 130b, both of which extend out of the base 120. The front end 130a is used to communicate with the opening 20 of the drug storage unit 1110, while the subcutaneous end 130b is used to penetrate into the subcutaneous.

As shown in FIG. 9c, the housing 100 is further provided with a cavity 30 including a first outlet 31 and a second outlet 32. The first outlet 31 is in sealed communication with the opening 20. Here, the sealed communication means that the cavity 30 and the drug storage unit 1110 are in communication with each other through the opening 20 and the first outlet 31 without drug leaking. The second outlet 32 is sealed by an elastic seal 40. When the front end 130a pierces the elastic seal 40, the infusion needle 130, the cavity 30, the opening 20 and the drug storage unit 1110 are in communication. Therefore, the drug can enter the infusion needle 130 from the drug storage unit 1110 to the subcutaneous end 130b or be infused subcutaneously, as shown in FIG. 9c.

Please continue to refer to FIG. 9a and FIG. 9b, in the embodiment of the present invention, the base 120 has three positions: an initial position, an intermediate position, and a working position. Among them, the intermediate position is set between the initial position and the working position. Since the infusion needle 130 is fixed on the base 120, in the embodiment of the present invention, the infusion tube structure also has the above three positions.

Preferably, in the embodiment of the present invention, when the base 120 is at initial position, the front end 130a does not pierce the elastic seal 40, so it is not communicated with the second outlet 32. When the base 120 reaches the intermediate position or the working position, the front end 130a pierces the elastic seal 40 communicating with the second outlet 32. At this time, the drug, along the cavity 30 and the infusion needle 130, flows from the drug storage unit 1110 to the subcutaneous end 130b.

At the beginning, the base 120 is at the initial position with the infusion needle 130 non-communication with the drug storage unit 1110. Therefore, the cavity of the infusion needle 130 is full filled with air. When leaving the factory, the non-communication between the infusion needle 130 and the drug storage unit 1110 can improve the flexibility of the setting position of the infusion needle 130, which optimizes the structural design of the infusion device.

After the base 120 reaches the intermediate position, the front end 130a pierces the elastic seal 40 in order to make the infusion needle 130 communicate with the drug storage unit 1110. At this time, when the infusion unit is activated, the drug can flow, along the infusion needle 130, to the subcutaneous end 130b, exhausting the air in the cavity of the infusion needle 130. Then, when the base 120 reaches the working position, the subcutaneous end 130b enter into subcutaneous to inject the drug into the body. Since the air in the infusion needle 130 has been exhausted earlier, no air will be infused into subcutaneous when the base 120 reaches the working position, thereby eliminating potential safety hazards.

In order to ensure that the infusion tube structure can reach different positions, the infusion device of the present invention is also provided with a first fastener 140 which is used to fasten the base 120 at the above-mentioned different positions. The type of the first fastener 140 includes one or more of hooks, holes, blocks, and slots. Preferably, in the embodiment of the present invention, the first fastener 140 is a hook.

Please continue to refer to FIG. 9b, in the embodiment of the present invention, the base 120 also includes a guide post 121. The position where the base 120 is fastened by the first fastener 140 is located on the guide post 121. For example, when the base 120 is fastened at position A, the base 120 is at the initial position; and when fastened at position B, the base 120 is at the intermediate position.

Please continue to refer to FIG. 9a, in the embodiment of the present invention, the infusion device further includes a fastening component 110 which is used to limit the position of the base 120. Therefore, the first fastener 140 is disposed on the fastening component 110. Preferably, in the embodiment of the present invention, a fastening arm 112 is provided on the fastening component 110. And the first fastener 140 is disposed on the fastening arm 112.

When the base 120 is at the initial position, the first fastener 140 is fastening at position A. Directly pressing the top of the base 120 with a finger makes the first fastener 140 fasten the guide post 121 at position B, so that the base 120 reaches the intermediate position.

It should be noted that the base 120 may not be provided with the guide post 121, but a structure capable of fastening with each other is provided on the side wall of the base 120, which is not specifically limited here, as long as the base 120 can reach different position.

Preferably, in the embodiment of the present invention, the use of the fastening component 110 can only fasten the base 120 at the initial position and the intermediate position. In addition, the base 120 cannot reach the working position due to the fastening component 110. At the same time, a second fastener 150 is provided on the housing 100 which is used to fasten the base 120 at position C, in order to make the base 120 fastened at the working position.

Figure 10:
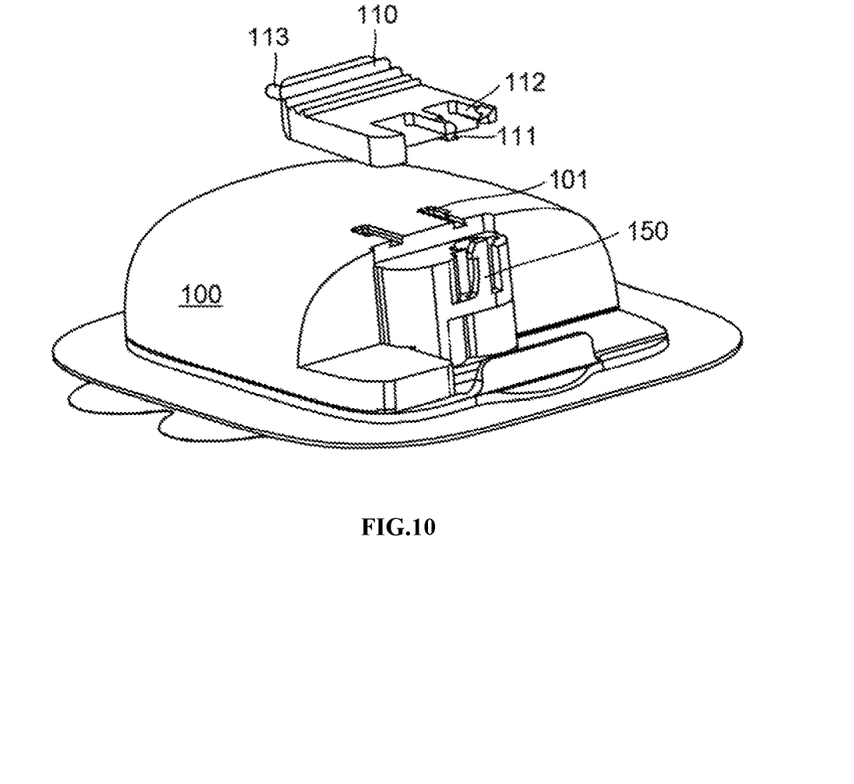
FIG. 10 is a schematic view of the fastening component separated from the housing according to an embodiment of the present invention.

FIG. 10 is a schematic view of the fastening component 110 separated from the housing 100 according to an embodiment of the present invention.

Figure 12:
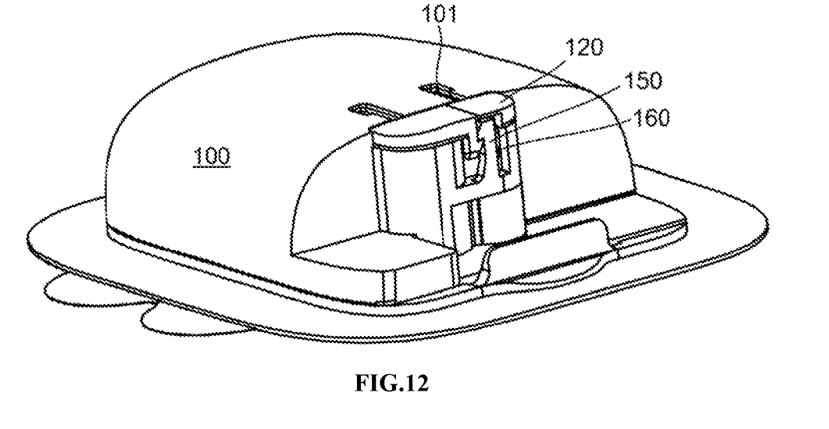

The fastening component 110 of the embodiment of the present invention includes a slider 111. The housing 100 is provided with a groove 101 where the slider 111 is arranged. The fastening component 110 can slide along the groove 101 to fasten the base 120 or release it. Preferably, in the embodiment of the present invention, after the sliding fastening component 110 releases the base 120, the fastening component 110 can be removed from the housing 100, as shown in FIG. 12.

Therefore, the working principle of the base 120 reaching these three positions in the embodiment of the present invention is as follows. At the beginning, the infusion device is not attached to the skin surface. And the first fastener 140 is fastening the guide post 121 at position A, so the base 120 is at the initial position. At this time, the front end 130a does not pierce the elastic seal 40, so that the infusion needle 130 is not in communication with the drug storage unit 1110. Then, directly pressing the top of the base 120 with a finger makes the first fastener 140 fasten the guide post 121 at position B, so the base 120 is in the intermediate position. Although the infusion device is still not attached to the skin surface, the front end 130a of the infusion needle pierces the elastic seal 40 making the infusion needle 130 communicate with the drug storage unit 1110. Therefore, the drug can flow in the cavity of the infusion needle 130 and exhaust air in the infusion needle 130. At this position, the subcutaneous end 130b does not extend or slightly extends out of the housing 100. Then attach the infusion device on the skin surface. And slide the fastening component 110 backward to release the base 120. Continue to press the top of the base 120 so that the second fastener 150 fastens the guide post 121 at position C. Therefore, the base 120 is in the working position, and the subcutaneous end 130b penetrates the subcutaneous. Obviously, the infusion needle 130 is communicated with the drug storage unit 1110, and the drug can be injected to subcutaneous.

Figure 11:
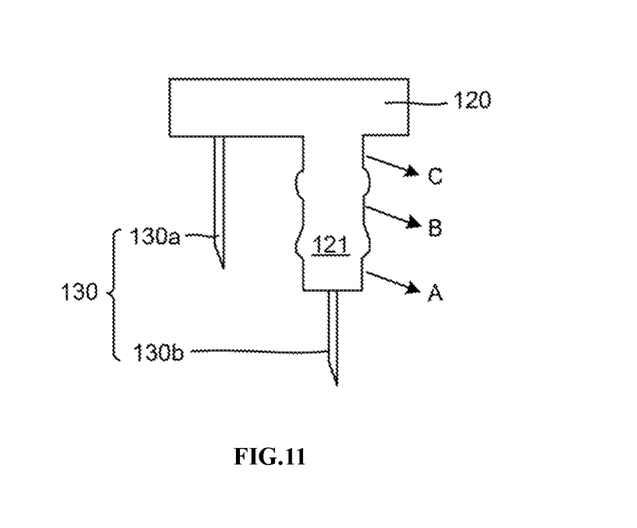
FIG. 11 is a schematic view of an infusion tube structure according to another embodiment of the present invention.

FIG. 11 is a schematic view of an infusion tube structure according to another embodiment of the present invention.

In another embodiment of the present invention, the infusion device may not be provided with the fastening component 110 and the second fastener 150, but the first fastener (not shown at this time) is directly provided on the housing 100. At this time, the initial position A, the intermediate position B and the working position C are all located on the guide post, as shown in FIG. 11. When the base 120 is at the initial position, the first fastener is fastening at position A. When the top of the base 120 is pressed, the base 120 moves downward, the first fastener is fastening at position B, helping the base 120 reach the intermediate position. Continue to press the top of the base 120, in order to make the base 120 continue to move downwards. The first fastener is fastening at position C, making the base 120 reach in the working position. This design reduces the number of structures in the infusion device and facilitates user operation.

FIG. 12 is a schematic view of the base 120 in the working position according to the embodiment of this present invention.

The infusion device also includes an elastic member 160 provided on the base 120 or on the housing 100. Preferably, in the embodiment of the present invention, the elastic member 160 is a spring provided on the housing 100, and a part of the guide post 121 is located in the hollow cavity of the spring (as shown in FIG. 9b). When the base 120 is in the working position, the elastic member 160 is compressed, thereby generating a resilient force.

In other embodiments of the present invention, the elastic member 160 may also be a structure such as elastic silicone, elastic sheet, etc., which is not specifically limited here. As in an embodiment of the present invention, the elastic member 160 is disposed on the base 120, and the elastic member 160 interacts with one structure of the housing 100 to generate a resilient force.

As mentioned above, when the base 120 is in the working position, the subcutaneous end 130*b* is pierced into subcutaneous. If the subcutaneous end 130*b* does not retract into the infusion device when the infusion device is torn off from the skin surface, the end of the subcutaneous end 130*b* is likely to scratch the skin, causing additional trauma and poor user experience. Therefore, the subcutaneous end 130*b* of the infusion needle can be retracted, by the resilient force of the elastic member 160, into the housing 100 before the infusion device is torn off, which avoids scratching the skin and improves user experience.

Preferably, in the embodiment of the present invention, the infusion device further includes an auxiliary resilient component 113 (as shown in FIG. 9*a* and FIG. 10) which is used to release the base 120. After the fastened base 120 is released, the base 120 can return to the intermediate position or the initial position under the action of the resilience of the spring.

The embodiment of the present invention does not limit the type of the auxiliary resilient component 113 and the manner or position for releasing the base 120. As in the embodiment of the present invention, the auxiliary resilient component 113 is provided at one end of the fastening component 110. The auxiliary resilient component 113 can be inserted into the housing 100 to change the position of the second fastener 150 to release the base 120. In another embodiment of the present invention, the auxiliary resilient component 113 can enter the inside of the housing 100 from a hole (not shown) provided on the top of the base 120, thereby changing the position of the second fastener and releasing the base 120. In still another embodiment of the present invention, an additional sliding button connected to the second fastener may be provided. The user can slide the sliding button with a finger to release the base 120.

It should be noted that, in other embodiments of the present invention, the manner in which the base 120 reaches different positions can also be automatically controlled by a program. Therefore, the user does not need to manually operate with a finger, which is not specifically limited here.

In summary, the present invention provides a unilateral-driven patch-type drug infusion device. The power unit outputs a controllable and stable driving force to drive the driving portion forward, thereby pushing the wheel teeth forward, avoiding the drug blockage. At the same time, before the infusion device is attached on the skin surface, the drug can exhaust the air in the infusion needle, preventing air from being infused into subcutaneous, which eliminates safety hazards and improves user experience.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A unilateral-driven patch-type drug infusion device, comprising:
    an infusion unit, comprising:
        a drug storage unit providing with an opening for drug flowing;
        a screw connected to a piston and a driving wheel provided with wheel teeth, wherein the driving wheel drives the screw to move by rotation, thereby pushing the piston, provided in the drug storage unit, forward;
        at least one driving unit cooperating with the driving wheel, wherein the driving unit includes at least one driving portion; and
        a power unit and a reset unit coupled to the driving unit, wherein:
            when the power unit outputs force on the driving unit, the driving unit rotates around a pivot shaft, driving the driving portion to push the wheel teeth, thus rotating the driving wheel;
            when the reset unit outputs a force on the driving unit alone, the driving unit performs a reset rotation without the driving portion pushing the wheel teeth, thus making the driving wheel stop rotating;
    a housing, where the infusion unit is provided, comprising a cavity providing with a first outlet and a second outlet, wherein the opening is in sealed communication with the first outlet while the second outlet is sealed by an elastic seal;
    an infusion tube structure, comprising a base and an infusion needle fixedly arranged on the base, wherein the base is located at a position which is an initial position, a working position, or an intermediate position set between the initial position and the working position; and
    a first fastener, which is used to fasten the base in order to limit the position of the base, wherein the infusion needle comprises a front end and a subcutaneous end, after the base reaches the intermediate position, the front end pierces the elastic seal in order to make the infusion needle communicate with the drug storage unit, when the base is at the intermediate position, the subcutaneous end does not extend out of the housing, at this time, when the infusion unit is activated, a drug can flow, along the infusion needle, to the subcutaneous end, exhausting the air in the infusion needle.

2. The unilateral-driven patch-type drug infusion device of claim 1, wherein
    the at least one driving unit comprises two driving portions, and under a cooperative operation of the power unit and the reset unit, the two driving portions alternately push the wheel teeth.

3. The unilateral-driven patch-type drug infusion device of claim 2, wherein
    the two driving portions alternately push the wheel teeth disposed on the driving wheel.

4. The unilateral-driven patch-type drug infusion device of claim 2, wherein
    the driving wheel comprises two sub-wheels provided with wheel teeth, and the two driving portions alternately push the wheel teeth disposed on the two sub-wheels.

5. The unilateral-driven patch-type drug infusion device of claim 1, wherein
    each of the power unit and the reset unit is a linear actuator.

6. The unilateral-driven patch-type drug infusion device of claim 5, wherein
    the linear actuators comprises a shape memory alloy.

7. The unilateral-driven patch-type drug infusion device of claim 1, wherein
    the reset unit at least comprises a spring, an elastic sheet, an elastic plate, an elastic rod, or elastic reset rubber.

8. The unilateral-driven patch-type drug infusion device of claim 7, wherein
    the at least one driving portion comprises one driving portion, and the reset unit is a spring.

9. The unilateral-driven patch-type drug infusion device of claim 1, wherein
the first fastener comprises one or more of hooks, holes, blocks, or slots.

10. The unilateral-driven patch-type drug infusion device of claim 9, further comprising
an elastic member arranged on the base or the housing, and when the base is in the working position, the elastic member is compressed.

11. The unilateral-driven patch-type drug infusion device of claim 10, further comprising
an auxiliary resilient component, which is used to release the base, therefore under an action of a resilient force of the elastic member, the base returns to the intermediate position or the initial position from the working position.

12. The unilateral-driven patch-type drug infusion device of claim 11, wherein
the base comprises a guide post, and the position where the base is fastened is located on the guide post.

13. The unilateral-driven patch-type drug infusion device of claim 12, wherein
the elastic member is a spring arranged on the housing, and a part of the guide post is located in a hollow cavity of the spring.

14. The unilateral-driven patch-type drug infusion device of claim 13, wherein
the first fastener is provided on the housing.

15. The unilateral-driven patch-type drug infusion device of claim 13, further comprising
a fastening component, wherein the first fastener is disposed on the fastening component.

16. The unilateral-driven patch-type drug infusion device of claim 15, wherein
a sliding block is provided on the fastening component while the housing is provided with a groove, the sliding block is arranged in the groove, and the sliding block slides along the groove to make the fastening component fasten or release the base.

17. The unilateral-driven patch-type drug infusion device of claim 15, wherein
at least one fastening arm is provided on the fastening component, and the first fastener is provided on the fastening arm.

18. The unilateral-driven patch-type drug infusion device of claim 17, wherein
a second fastener is provided on the housing, the first fastener is used to fasten the base at the initial position or the intermediate position while the second fastener is used to fasten the base at the work position.

19. The unilateral-driven patch-type drug infusion device of claim 1, wherein
both the front end and the subcutaneous end extend out of the base, wherein:
when the base is at the initial position, the front end is not communicated with the second outlet;
when the base reaches the working position, the front end pierces the elastic seal to communicate with the second outlet, and the drug, along the cavity, flows from the drug storage unit to the subcutaneous end.

* * * * *